United States Patent
Firestone et al.

[11] Patent Number: 6,001,868
[45] Date of Patent: Dec. 14, 1999

[54] INDOLE-3-CARBINOL (I3C) DERIVATIVES AND METHODS

[75] Inventors: Gary L. Firestone; Leonard F. Bjeldanes; Carolyn M. Coyer, all of Berkeley, Calif.

[73] Assignee: The Regents of the University of California, Oakland, Calif.

[21] Appl. No.: 08/865,920

[22] Filed: May 30, 1997

[51] Int. Cl.[6] .......................... A01N 43/38; A61K 31/405
[52] U.S. Cl. ........................... 514/415; 514/419; 424/9.2; 435/6; 435/7.72; 435/7.8; 435/7.9; 435/7.91; 435/21
[58] Field of Search ..................... 514/415, 419; 424/9.2; 435/6, 7.72, 7.8, 7.9, 7.91, 21

[56] References Cited

U.S. PATENT DOCUMENTS 5,895,797  4/1999  Arffman et al. ..................... 514/415

OTHER PUBLICATIONS

Chemical Abstracts vol. 103:171535 c (von Angerek et al.), 1985
Chemical Abstracts vol. 115:200908 g (Bradlow et al.), 1991.
Chemical Abstracts vol. 123:339726 l (Ikeda et al.), 1995.
Ng et al—Eur. J. Pharmacol. vol. 264(1) pp. 1–12 (Abstract), 1994.

*Primary Examiner*—Frederick Krass
*Attorney, Agent, or Firm*—Richard Aron Osman

[57] ABSTRACT

The invention provides methods and compositions relating to novel bioactive derivatives of indole-3-carbinol (I3C), including pharmaceuticals comprising a pharmaceutically acceptable excipient and a compound of the general formula:

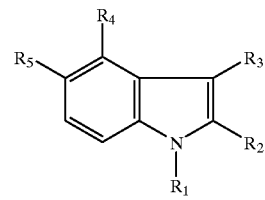

which inhibits tumor cell growth. Methods of inhibiting targeted cell growth include contacting a target cell with a disclosed compound under conditions whereby the growth the target cell is inhibited, and methods for evaluating the growth inhibitory activity of the compounds include contacting a cell with an effective amount of the compound and measuring the CDK6 expression in the cell, wherein a reduction in CDK6 expression correlates with the growth inhibitory activity of the compound.

3 Claims, No Drawings

INDOLE-3-CARBINOL (I3C) DERIVATIVES AND METHODS

The research carried out in the subject application was supported in part by grants from the US Army Medical Research Command (Contract No. RP950844). The government may have rights in any patent issueing on this application.

INTRODUCTION

1. Field of the Invention

The invention relates to indole-3-carbinols and their bioactivity

2. Background of the Invention

More than 40,000 women die each year of metastatic breast cancer in the United States. Endocrine therapy, in particular anti-estrogen therapy, remains a major option for treatment of such patients, and results in complete plus partial response rates of 30%. This response rate results from the fact that the growth of approximately one-third of breast cancers is stimulated by estrogen, which is a natural hormone produced in women. Treating patients with anti-estrogens, such as tamoxifen, will slow the growth of these estrogen dependent tumors. Postmenopausal status, a prolonged disease-free interval, and positive estrogen and progesterone receptors are all associated with an increased response to endocrine therapy. The use of additive hormonal therapy, specifically antiestrogens, progestins, and aromatase inhibitors, have replaced surgical ablative procedures in the majority of estrogen receptor positive patients; with the most favorable therapeutic index associated with therapies that use antiestrogens (55). For patients that are estrogen receptor negative and a subset of patients that are estrogen receptor positive, the best current approach to treating breast cancers that do not require estrogen for their growth is by surgical removal of the tumors. Unfortunately, even for the patients that respond to and can benefit from tamoxifen therapy, there are many detrimental side effects including the ability of breast cancer cells to become resistant to tamoxifen, an increase in the potential for ovarian tumors and an increased risk of osteoporosis. Some of these side effects are due to tamoxifen acting as an estrogen agonist in some tissues and remaining an estrogen antagonist in other tissues.

Indole-3-carbinol (I3C) is a naturally occurring component of Brassica vegetables, such as cabbage, broccoli, and Brussels sprouts. Exposure to dietary I3C markedly reduces the incidence of spontaneous and carcinogen-induced mammary tumors in rodents and, as disclosed herein, exhibits potent growth inhibitory activity in human breast cancer cells in vitro by inducing a G1 arrest of the cell cycle. A recent screen of 90 potential chemopreventative agents in a series of 6 short term bioassays relevant to carcinogen-induced DNA damage, tumor initiation and promotion, and oxidative stress, revealed I3C to be one of only 8 compounds that tested positive in all assays (1). Indeed, I3C administered in the diet or by oral intubation prior to treatment with carcinogen reduced the incidence of 7,12-dimethyl-benz($\alpha$) anthracene (DMBA)-induced mammary tumors in rodents by 70–80% (2). In another study, I3C administered to rats prior to and during DMBA or methylnitrosourea treatment reduced mammary tumor incidence by as much as 95% or 65%, respectively (3). Consistent with these results, supplementation of a purified diet with cabbage or broccoli, both vegetables are good sources of I3C, also resulted in decreased mammary tumor formation in DMBA-treated rats (4). Also, in a long term feeding experiment, in which female mice consumed synthetic diets containing I3C at 0, 500 or 2000 p.p.m., spontaneous mammary tumor incidence and multiplicity were significantly lower (ca. 50% reduction) at both doses of I3C compared to untreated control animals, and tumor latency was prolonged in the high dose group (5). I3C also has anticarcinogenic effects on other cancer types, such as hepatic derived tissues (6–9), and can reduce benzo[a]pyrene-induced neoplasia of the forestomach (2). Because of the well documented cancer protective effects of I3C, along with its low toxicity, and its wide availability, this dietary indole is currently undergoing at least two different phase I clinical trials as a cancer chemotherapeutic and preventive agent (10).

I3C has been shown to have an antiestrogenic biological activity when added to the diet. For example, oral administration of I3C to humans at doses of around 500 mg daily for one week produced an increase in estradiol 2-hydroxylation of approximately 50% in both men and women (11). I3C also increased the levels of estradiol hydroxylation activity in female rats (12). I3C can, in some systems, display an antiestrogenic growth suppressive effect. For example, long term treatment (up to six weeks) with 50 $\mu$M I3C blocked the estradiol-induced proliferation of high density cultures (confluency for 1 weeks or longer) of human MCF7 breast cancer cells (13).

A major complication in interpreting the physiological results is that I3C is extremely unstable in acidic solution and it does not completely survive exposure to gastric acid (14). I3C is converted into several natural indole derivatives with biological activities. The acid reaction mixture of I3C is composed of five major components which are resolvable by HPLC (15). Sensitive analytical methods reveal that I3C is converted to several indole derivatives in acid conditions and in the intestinal contents of rats fed on a basal diet and treated orally with I3C (15–19), suggesting that these I3C derivatives may mediate the anti-estrogenic effects of I3C. I3C is converted into biologically active components such as its dimer 3,3'-diindolylmethane (DIM) and indolo[3,2-b] carbazole (ICZ) through an acid-catalyzed reaction occurring in the low-pH environment of the stomach (17). ICZ is also produced, presumably from the nutritive indole, tryptophan, as a metabolic product of intestinal bacteria (19).

A general picture has emerged indicating that many, if not all, of the long term antiestrogenic biological activities of I3C result from the actions of one of its acid conversion products (15–19). For example, ICZ is a potent inhibitor of several estrogen-dependent responses including growth inhibition of high density cultures of human breast cancer cells (20), and ICZ inhibited [$^3$H]thymidine uptake, nuclear progesterone and ER binding, and CAT activity in MCF7 cells transfected with the estrogen-responsive vit-CAT reporter plasmid. However, ICZ exhibited only a very weak affinity for the estrogen receptor suggesting that its not a direct estrogen antagonist. Further studies showed that ICZ likely mediates its antiestrogenic effects through interactions with Ah (dioxin) receptor (21). ICZ competitively binds to the Ah receptor, which then translocates to the nucleus and induces P450 CYP1A1 gene expression which has been shown to alter estrogen metabolism (21). ICZ is the most potent Ah receptor agonist among the characterized I3C derived compounds. In fact, I3C itself has a particularly low affinity for the Ah receptor (Kd of 27 $\mu$M), compared to ICZ's high affinity (Kd of 190 pM) and the relatively moderate affinity of DIM (Kd of 90 nM) for the Ah receptor (17). Thus, I3C per se does not mediate any of its activities directly through the Ah receptor, and its mechanism of signal transduction and direct target genes are unknown. Other investigators have shown that the predominant I3C conversion product DIM was highly effective in reducing DMBA-induced mammary tumors, but DIM apparently was not consistently as effective as I3C (2).

We disclose herein that treatment of a human breast cancer cells with I3C induces a reversible growth arrest in an estrogen independent manner, resulting from a G1 cell cycle arrest. The G1 arrest in cell cycle progression correlates with a significant loss of CDK6 protein, a key cyclin dependent kinase involved in progression through the G1 phase of the cell cycle. Our data indicate that I3C itself, and not its acid breakdown products, is a potent anti-tumor agent, and that stable derivatives of I3C may be used to inhibit the growth of estrogen-dependent or independent breast cancer cells and other types of cancer cells that reveal induced CDK6.

SUMMARY OF THE INVENTION

The invention provides methods and compositions relating to novel bioactive compositions. The compositions find particular use as agents for inhibiting cell growth. In one embodiment, the invention provides pharmaceutical compositions comprising a pharmaceutically acceptable excipient and a compound of the general formula:

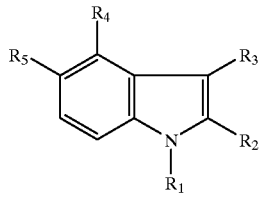

or a pharmaceutically acceptable salt or ester thereof, wherein:

$R_{1-5}$ are independently selected from the group consisting of substituted or unsubstituted alkyl, alkenyl, alkynyl, aryl, heteroalkyl, heteroaryl, and acyl substituents wherein said compound inhibits tumor cell growth and said compound is other than indole-3-carbinol (I3C), 3,3'-diinodolylmethane (DIM) and indolo[3,2-b] carbazole (ICZ).

In various preferred embodiments, at least one of $R_4$ and $R_5$ is an electron withdrawing substituent such as ammonium, nitrile, halogen, nitro, sulfhydril, and hydroxyl groups, $R_3$ is an electron donating substituent such as carboxylate, alkylhydroxy, alkylester and alkylether, $R_2$ comprises a substituted or unsubstituted aromatic moiety, and $R_1$ is selected from the group consisting of substituted or unsubstituted oxide, amino and carbonyl functional groups.

Preferred compounds are other than a natural gastric acid metabolite of I3C, inhibit cell growth in an estrogen-independent manner, and particularly, by inhibiting a CDK6 activity, and demonstrate enhanced metabolic stability over I3C. The compositions may advantageously further comprise an antiestrogen, such as tamoxifen, ICI 164384 and raloxifene.

In addition, the invention provides methods of inhibiting targeted cell growth. In one embodiment, such methods comprise contacting a target cell with a compound of the foregoing general formula, or a pharmaceutically acceptable salt thereof, wherein $R_{1-5}$ are independently selected from the group consisting of substituted or unsubstituted alkyl, alkenyl, alkynyl, and aryl; and wherein said compound inhibits tumor cell growth and said compound is other than I3C, DIM and ICZ, under conditions whereby the growth the target cell is inhibited.

The invention also provides methods for evaluating the growth inhibitory activity of a compound of the foregoing general formula or an I3C derivative. In one embodiment, these methods comprise the steps of contacting a cell with an effective amount of the compound and measuring the CDK6 expression in the cell, wherein a reduction in CDK6 expression correlates with the growth inhibitory activity of the compound.

DESCRIPTION OF PARTICULAR EMBODIMENTS OF THE INVENTION

The term substituted or unsubstituted alkyl is intended to encompass alkoxy, cycloalkyl, heteroalkyl, etc. Similarly, the term substituted or unsubstituted aryl is intended to encompass aryloxy, arylalkyl (including arylalkoxy, etc.), heteroaryl, arylalkynyl, etc.; the term substituted or unsubstituted alkenyl is intended to analogously encompass cycloalkenyl, heteroalkenyl, etc.; etc. In prefered embodiments, the subsitituted or unsubstituted alkyl is selected from heteroalkyl (including alkoxy, etc.), cycloalkyl, acylalkyl, etc.; the subsitituted or unsubstituted alkenyl is selected from heteroalkenyl, cycloalkenyl, acylakenyl, etc.; the subsitituted or unsubstituted alkynyl is selected from heteroalkynyl, cycloalkynyl, acylakynyl, etc.; and the subsitituted or unsubstituted aryl is selected from heteroaryl (including aryloxy, heteroaryl, heteroaryloxy, heteroarylalkyl, heteroarylalkyoxy, heteroarylheteroalkyl, heteroarylalkenyl, heteroarylalkyl and heteroaryloxyheteroalkyl, etc.), arylcycloalkyl, arylcycloalkenyl, aryloxycycloalkyl, arylalkyl, arylalkoxy, arylheteroalkyl, aryloxyalkyl, aryloxyheteroalkyl, etc.

The invention provides methods of making the subject compounds and compositions. Generally, the compounds of the invention, including synthetic derivatives of I3C, are prepared by methods standard in the art of chemical synthesis, characterized for their purity, chemical properties and structure, then examined for their biological properties including growth suppression, effects on CDK6 protein levels and biological stability. For example, the structures of new I3C derivatives are identified by analysis of spectral and chemical properties including low resolution mass spectrometry and ultraviolet spectroscopy, and the molecular formulae obtained by analysis of the high resolution mass spectrum (15).

The instability of I3C in aqueous solutions (15, 17) derives form the fact that I3C is a vinylogous hemiaminal, and as such it undergoes facile dehydration to the 3-methyleneindoleninium cation. This cation readily reacts with various nucleophiles including I3C.

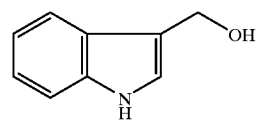

One preferred class of I3C derivatives with enhanced therapeutic indices are prepared by introducing substituents onto the indole nucleus that modify the ease with which the indolenium compound is produced (class A); a second class B is modeled after metabolic products of I3C and related natural compounds produced in vivo; and a third class C provides modified lipid solubility of the hydroxymethyl indole nucleus.

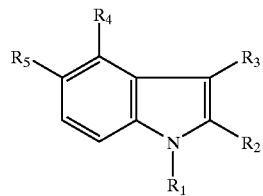

Class A: $R_1$=—$CH_3$, —$CH_2\phi$, —COR, etc.; $R_3$=—CHOHR, —$CH_2R$, —$CH_2SO_2R$, —$CH_2NHR$, etc.
Class B: -3-methylinole oligomers; $R_3$=—$CH_2SR$, etc.
Class C: $R_4$ or $R_2$=—$NO_2$, —O-Methyl, —Cl, alkyl, aryl, etc.

For example, N,O-diacetyl-indole-3-carbinol and derivatives thereof have been found to be particular effective inhibitors of cell growth.

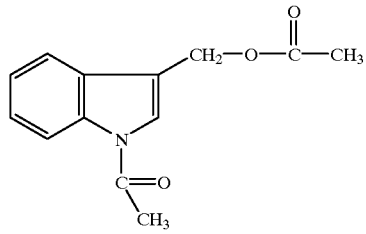

Several examples of the chemical synthesis of I3C derivatives from gramine are shown below.

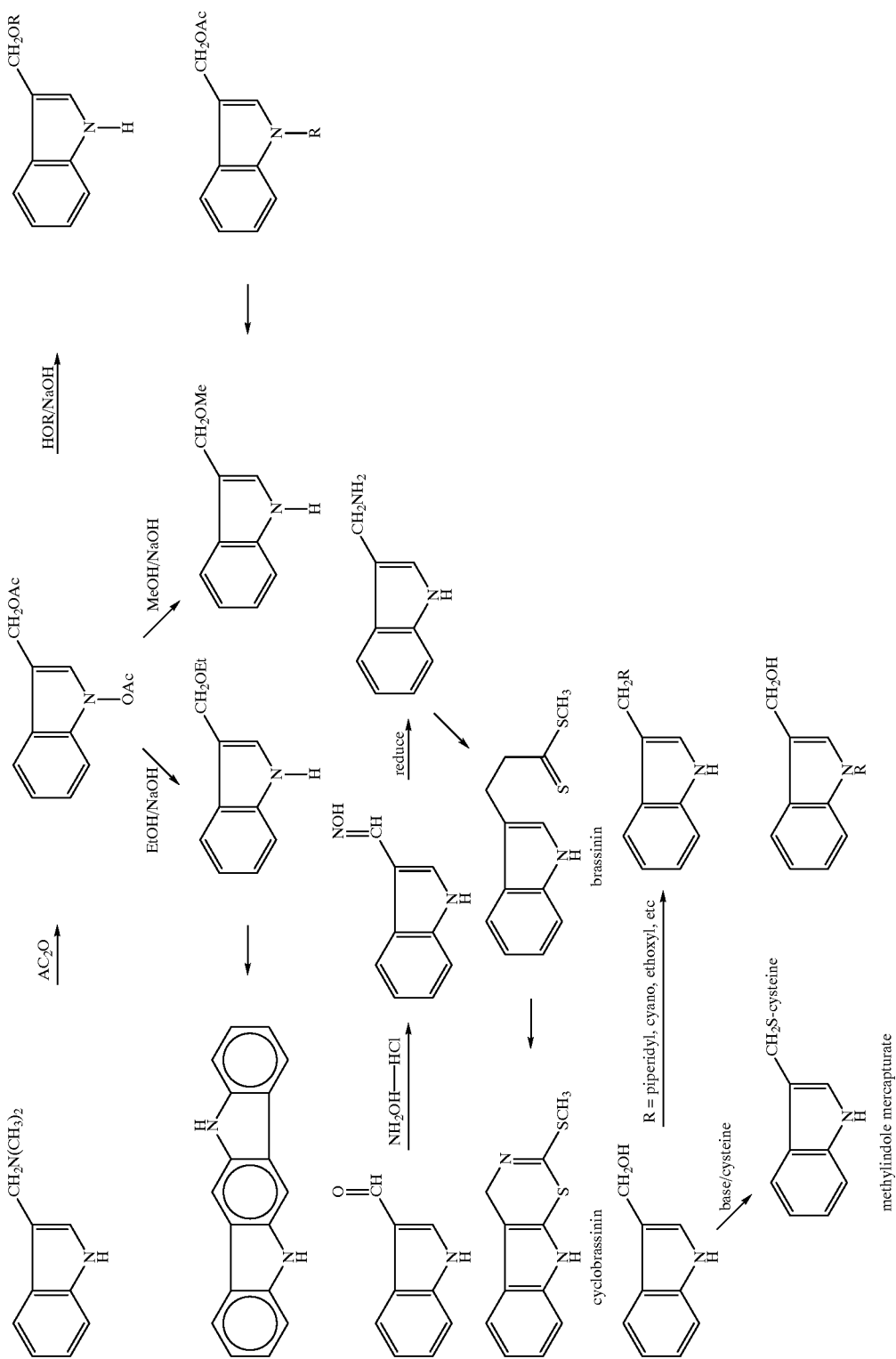

TABLE

Exemplary compounds with mutiple bioactive species.

| Compounds | R$_1$ | R$_2$ | R$_3$ | R$_4$ | R$_5$ |
|---|---|---|---|---|---|
| HBC001 | H, acyl, lower alkyl, phenyl, meth/phenoxyl | H | CH$_2$OR, R=lower alkyl, phenyl, acyl | H | H |
| HBC002 | H, acyl, lower alkyl, phenyl, meth/phenoxyl | H | H | H | acyl, nitro, halogen |
| HBC003 | H | H | CH$_2$OR R=H, lower alkyl, phenyl, acyl | H | acyl, nitro, halogen |
| HBC004 | H, acyl, lower alkyl, phenyl, meth/phenoxyl | H | H | acyl, nitro, halogen | H |
| HBC005 | H | H | CH$_2$OR R=H, lower alkyl, phenyl, acyl | acyl, nitro, halogen | H |
| HBC006 | H, acyl, lower alkyl, phenyl, meth/phenoxyl | H | H | alkyl, phenyl | H |
| HBC007 | H | H | CH$_2$OR R=H, lower alkly, phenyl, acyl | alkyl, phenyl | H |
| HBC008 | H, acyl, lower alkyl, phenyl, meth/phenoxyl | OR, R=lower alkyl, phenyl, acyl | H | H | H |
| HBC009 | H | OR, R=lower alkyl, phenyl, acyl | CH$_2$OR R=H, lower alkyl, phenyl, acyl | H | H |
| HBC010 | H, acyl, lower alkyl, phenyl, meth/phenoxyl | alkyl, phenyl | H | H | H |
| HBC011 | H | alkyl, phenyl | CH$_2$OR R=H, lower alkyl, phenyl, acyl | H | H |
| HBC012 | H | H | H | acyl, nitro, halogen | acyl, nitro, halogen |

Substitution of the hydrogen atom on the indole nitrogen with electron donating or withdrawing groups may be used to modify the rate of acid catalyzed formation of the methyleneindoleninium cation. Acyl derivatives at R1 may be prepared by treating the indole with the corresponding anhydrides (46) and alkyl derivatives at R1 prepared by treating the indole-3-carboxaldehyde with alkyl halide followed by mild reduction of the product to the alcohol (47). Another method to modify reactivity of the indole is to incorporate electron donating or electron withdrawing groups at R5 which affect electron density on the indole nitrogen via conjugation. Indoles substituted at this position with acyl, nitro, halogen or alkyl groups may be prepared from the appropriate phenylcarbonyl precursor used in the Fisher indole synthesis or by manipulation of appropriate available precursor indoles. Reactivity of the C-3 hydroxyl group can be modified directly by proper choice of R3. Ether and secondary amine derivatives may be prepared by treatment of N,O-diacetyl I3C with the desired alcohol or amine (46). C-3 secondary alcohols are available from the corresponding ketones by mild reduction.

Established in vivo products of I3C are various indole oligomers, oxidation products, and glutathione metabolites. Indole oligomers may be prepared by intermediate scale treatment of I3C with simulated gastric acid and then purification of the products by chromatography (46). The pentacyclic aromatic derivative, ICZ, may be prepared by the Fisher indole method with 1,4-cyclohexadione as the carbonyl component (17). Glutathione conjugates may be prepared by treatment of I3C with the desired sulfur derivative in basic solution (48).

An additional group of sulfur containing indole products from Brassica plants is brassinin and related compounds (49). Brassinin may be prepared synthetically from 3-(aminomethyl)indole by treatment with CS2 and methyliodide. Cyclobrassinin and similar compounds may be prepared from brassinin-type precursors by a pyridinium bromide perbromide mediated cyclization (50). Spirobrassinin and related compounds may be prepared from brassinin or related substances by treatment with thionyl chloride (49).

Indole derivatives with modified lipid solubilities may be prepared by appropriate choice of R4 and R2. Alkyl and aryl substitution at these sites increase the lipophilicity of the product, and hydroxy alkyl substitution increase the hydrophilicity of the product, both without affecting intrinsic reactivity. The products may be prepared by selection of the desired substituent in the Fisher indole precursor or via the Vilsmeier 3-carboxaldehyde prepared from the available substituted indole (47).

Occasionally, the substrates for the transformations described herein may contain functional groups (for example, amino, hydroxy or carboxy) which are not immediately compatible with the conditions of the given reaction. In such cases, these groups may be protected with a suitable protective group, and this protective group removed subsequent to the transformation to give the original functionality using well know procedures such as those illustrated in T. W. Greene and P. G. M. Wuts, Protective Groups in Organic Synthesis, Second Edition, John Wiley & Sons, Inc., 1991.

The compounds used as initial starting materials in this invention may be purchased from commercial sources or alternatively are readily synthesized by standard procedures which are well know to those of ordinary skill in the art.

Some of the compounds of the invention may exist as stereoisomers, and the invention includes all active stereoisomeric forms of these compounds. In the case of optically active isomers, such compounds may be obtained from corresponding optically active precursors using the procedures described above or by resolving racemic mixtures. The resolution may be carried out using various techniques such as chromatography, repeated recrystallization of derived asymmetric salts, or derivatization, which techniques are well known to those of ordinary skill in the art.

The compounds of the invention which are acidic or basic in nature can form a wide variety of salts with various inorganic and organic bases or acids, respectively. These salts must be pharmacologically acceptable for administration to mammals. Salts of the acidic compounds of this invention are readily prepared by treating the acid compound with an appropriate molar quantity of the chosen inorganic or organic base in an aqueous or suitable organic solvent and then evaporating the solvent to obtain the salt. Acid addition salts of the basic compounds of this invention can be obtained similarly by treatment with the desired inorganic or organic acid and subsequent solvent evaporation and isolation.

The compounds of the invention may be labeled in a variety of ways. For example, labeled subject compounds find use in a variety of in vitro and in vivo assays, including diagnostic assays, e.g. radioligand displacement assays. Accordingly, the invention provides the subject compounds and compositions comprising a detectable label, which may be spectroscopic (e.g. fluorescent), radioactive, etc. Similarly, the compounds may be advantageously joined, covalently or noncovalently, to a wide variety of joined compounds which may provide pro-drugs or function as carriers, labels, adjuvents, coactivators, stabilizers, etc. Hence, compounds having the requisite structural limitations encompass such compounds joined directly or indirectly (e.g. through a linker molecule), to such joined compounds.

The subject compositions are demonstrated to have pharmacological activity in in vitro and in vivo assays, e.g. are capable of specifically modulating a cellular physiology to reduce an associated pathology or provide or enhance a prophylaxis. Preferred compounds are capable of specifically inhibiting cell growth. Established cell and animal models to evaluate such bioactivity are well-known in the art.

Particularly suitable assays for I3C derivatives include evaluating their ability to induce a G1 cell cycle arrest and to inhibit CDK6 protein levels in cultured MCF7 breast cancer cells. For the cell proliferative asssays, we have sucessfully employed several methods that we have previously described for rodent mammary tumor cells (44, 51). Briefly, human MCF7 breast cancer cells are cultured at subconfluency in medium supplemented with 10% fetal bovine serum and 10 $\mu$g/ml insulin. The breast cancer cells are treated with a ranges of doses (generally 1 nM to 1 mM) of individual I3C-derivatives and I3C as a positive control and the DIM or ICZ acid derivatives of I3C (that do not suppress growth) as negative controls for various times up to 120 hours. The incorporation of [$^3$H]thymidine (in a two hour pulse) into 10% trichloroacetic acid precipitable material are used to monitor and quantitate DNA synthesis and provides a direct measure of the proliferative state of the cells. Flow cytometry analysis of nuclear DNA content after fluorescence staining with propidium iodide is used to confirm that a given I3C derivative induces a G1 block in cell cycle progression (44). Our results indicate that within the first 96 hours exposure to I3C, the breast cancer cells show a gradual change in the DNA content of the nuclear population from one in which the cells are in all phases of the cell cycle to one in which virtually all of the mammary cells are arrested with a G1-like 2n content of DNA, whereas I3C derivatives of enhanced efficiency require less time to induce cell cycle arrest.

Cancer cells are also treated with combinations of indole-derivatives and either steroidal or nonsteroidal anti-estrogens, such as tamoxifen, ICI 164384 and raloxifene (39, 52), at both suboptimal and optimal doses to determine the ability of a given I3C derivative to syngerize with the anti-estrogens in the growth suppression response. Hence, the effects of the indole derivatives on estrogen receptor levels, ligand binding activity and responsiveness are examined. For example, MCF7 cells are transiently transfected with the ERE-vit-CAT reporter plasmid, which contains three estrogen responsive elements, and the cells monitored for changes in estrogen regulated CAT activity. For comparison, the effects of the I3C derivatives on growth of the estrogen-non-responsive MDA-MB-231 breast cell line are examined. One of the characterized I3C acid products, ICZ acts as an antagonist of Ah receptor activity at low doses. Therefore, purified indole derivatives is also assayed in MCF7 cells for Ah receptor affinity, activation of Ah receptor binding to DNA, and activation of an Ah receptor-responsive CAT reporter (17).

Our finding that I3C inhibits the protein levels of the CDK6 cell cycle component provides a unique molecular assay to determine the ability of a given I3C derivative to induce a cell cycle arrest of cancer cells. For example, I3C derivatives may be analyzed by western blot to determine the level of CDK6 protein produced in treated or untreated human MCF7 breast cancer cells. In particular, cells are treated with varying concentrations, varying times alone or in the presence of particular sets of anti-estrogens; treatment with I3C may be used as a positive control. The cell extracts are then electrophoretically fractionated in SDS polyacrylamide gels, blotted onto nitrocellular membranes, the blotted proteins probed with CDK6 antibodies and the CDK6 protein visualized by autoradiography. Other G1 acting cell cycle genes may be examined to confirm that a given I3C derivative is acting similarly to I3C itself. For example, the levels of the other cyclin dependent kinases (CDK2 and CDK4), cell cycle activators (cyclin D1, D2, D3 and E) or cell cycle inhibitors (p15, 16, p21 or p27) that function at discrete times within G1 may be assessed in indole treated or untreated MCF7 breast cancer cells. Except for p21 at long times of indole treatment, I3C does not significantly alter the expression of these other cell cycle components.

Our novel observation that I3C coordinately inhibits the growth and reduces CDK6 protein levels of cultured human breast cancer cells indicates CDK6 protein levels is a diagnostic marker for the effectiveness of indole treatment on the suppression of the growth of breast cancer cells and other types of cancer cells that respond to the synthetic I3C derivatives. For this assay, small tissue samples of breast tumor (or other cancer types) may be tested for CDK6 protein levels by indirect immunofluorescence using polyclonal or monoclonal CDK6 antibodies that recognize the human CDK6 protein. The CDK6 protein is nuclear associated and the fluorescence signal may be observed on a single cell level. Also, normal breast tissue can be assayed similarly since only a few cells are needed for the assay. Alternatively, total RNA can be extracted from small samples of tumors and RT-PCR used to determine the presence of CDK6. However, this transcript assay requires larger tissues samples and we have recently discoverd that the level of CDK6 transcripts is relatively low in comparison to the protein levels. Patients with detectable CDK6 proteins are therefore candidates for treatment with particular synthetic I3C derivatives or with combinations of anti-estrogens and I3C derivatives if the patient's tumor cell samples are also estrogen receptor positive.

I3C dervatives that inhibit the proliferation of MCF7 cell cultures may be tested for their ability to suppress tumor growth. In one example of this assay, MCF7 cells are inoculated into nude athymic mice and effects on tumor growth and morphology determined as we have previously described for DMBA induced rodent mammary tumors (53, 54). To monitor the tumor formation, approximately two million cells are injected subcutaneously into the flanks of nude athymic mice (54). Control inoculations contain saline vehicle but no cells. The inoculated mice are either fed with particular synthetic derivatives of I3C supplemented diets (250–2500 ppm) or chronically injected with the synthetic indole derivatives (40–600 mg I3C/kg body weight), or with a vehicle control, every 48 hours starting with the day of mammary cell inoculation. To encompass I3C derivatives which disrupt tumor formation or latency period before the tumors have reached a palpable size (approximately 0.5 cm in diameter), tumor diameters of the treated and untreated mice are monitored twice a week using a calapiter over a six week time course. Depending on these results, in vivo disruption of the normal tumor growth pattern or of the growth suppressing effects of the I3C derivatives are monitored by determining bromodeoxyuridine (BUdR) labeling index for DNA synthesis (by BUdR antibody immunostaining). The in vivo stability, clearance rate and tissue uptake of a particular I3C derivative may be monitored using radioactive forms of the compounds. The growth suppressing effects of combinations of indoles and tamoxifen on MCF7-derived tumors may also be further evaluated in athymic mice.

The morphology of excised tumor cells may be analyzed histochemically (53, 54). Residual tumors may also be dispersed as single cell suspensions with collagenase and tested for appropriate in vitro growth response to indoles on plastic substratum as well as in soft agar to monitor anchorage independent growth. In addition, the level of CDK6 protein may be tested in the tumor samples by western blots or by indirect immunofluorescence.

The invention provides methods of using the subject compounds and compositions on cells in situ (residing within the host) to treat disease or provide medicinal prophylaxis, to downregulate CDK6 expression in a cell, to reduce cell growth in vitro or in a host, etc. For use in methods applied to cells in situ, the compositions frequently further comprise a physiologically acceptable excipient and/ or other pharmaceutically active agent to form pharmaceutically acceptable compositions. Hence, the invention provides administratively convenient formulations of the compositions including dosage units which may be incorporated into a variety of containers. The subject methods of administration generally involve contacting the cell with or administering to the host an effective amount of the subject compounds or pharmaceutically acceptable compositions. The compositions and compounds of the invention and the pharmaceutically acceptable salts thereof can be administered to a host in any effective way such as via oral, parenteral or topical routes. Generally, the compounds are administered in dosages ranging from about 2 mg up to about 2,000 mg per day, although variations will necessarily occur depending on the disease target, the host, and the route of administration. Preferred dosages are administered orally in the range of about 0.05 mg/kg to about 20 mg/kg, more preferably in the range of about 0.05 mg/kg to about 2 mg/kg, most preferably 0.05 to about 0.2 mg/kg of body weight per day. preferably in the range of about 0.05 mg/kg to about 0.2 mg per kg of body weight per day.

In one embodiment, the invention provides the subject compounds combined with a pharmaceutically acceptable excipient such as sterile saline or other medium, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents. In another embodiment, the invention provides the subject compounds in the form of a pro-drug, which can be metabolically converted to the subject compound by the recipient host. A wide variety of pro-drug formulations are known in the art. The compositions may be provided in any convenient form including tablets, capsules, lozenges, troches, hard candies, powders, sprays, creams, suppositories, etc. As such the compositions, in pharmaceutically acceptable dosage units or in bulk, may be incorporated into a wide variety of containers. For example, dosage units may be included in a variety of containers including capsules, pills, etc.

The compositions may be advantageously combined and/ or used in combination with other therapeutic or prophylactic agents, different from the subject compounds. In many instances, administration in conjunction with the subject compositions enhances the efficacy of such agents. For example, the compounds may be advantageously used in conjuction with other anti-neoplastic agents including alkylating agents known in the art such as nitrogen mustards, ethylenimines and methylmelanines, alkyl sulfonates, nitrosoureas and triazenes; antimetabolites such as folic acid analogs, pyrimidine analogs and purine analogs; natural inhibitors such as vinca ankaloids, epipodophylotoxins, antibiotics and enzymes; homones and antagonists such as adrenocorico steroids, progestins, estrogens and antiestrogens, androgens and antiandrogens, gonadotropin and releasing hormone analogs; etc.; and mixtures thereof, see e.g. Goodman & Gilman's The Pharmacological Basis of Therapeutics, $9^{th}$ Ed., 1996, McGraw-Hill, esp. Chabner et al., Antineoplastic Agents at pp. 1233.

The following examples are offered by way of illustration and not by way of limitation.

EXAMPLES

I3C acts as a potent growth inhibitor of human breast cancer cells in an estrogen independent manner: MCF7 human breast cancer cells were cultured at subconfluency in medium supplemented with 10% fetal bovine serum and 10 µg/ml insulin and then treated with several concentrations of I3C (0, 10 µM, 30 µM, 60 µM, 100 µM and 300 µM) for 48 hours. I3C strongly inhibited [$^3$H]thymidine incorporation in MCF-7 cell cultures, which provides a direct measure of the proliferative state of the cells, in a dose dependent manner, with half-maximal response at 30 µM I3C. At 300 µM I3C, cell proliferation was maximally inhibited and cell morphology was changed to a more elongated phenotype; however, at 100 µM I3C, the cells were near maximally growth arrested but with no morphology change. Therefore, 100 µM I3C was routinely used in the remainder of our experiments. Importantly, exposure to the two characterized acid products of I3C, the DIM oligomer and ICZ, failed to suppress the growth of MCF7 cell growth. Time course studies of I3C addition and withdrawal demonstrated that the I3C growth suppression of MCF-7 breast cancer cells is completely reversible, demonstrating that this compound does not affect cell viability. Also, prolonged exposure (5 days) to I3C did not result in any detectable cell death. Analysis of DNA synthesis over a 120 hour time course revealed that 100 µM I3C inhibited [$^3$H]thymidine incorporation by 80% after 72 hours and by greater than 90% after 96 hours of treatment. Within 48 hours of I3C withdrawal from 48 or 72 hour I3C-treated cells, the rate of [$^3$H]thymidine incorporation was approximately equivalent to untreated cells.

Several lines of evidence demonstrate that I3C suppresses the growth of human breast cancer cells independent of any effects on estrogen receptor responsiveness. I3C dose dependently inhibited [$^3$H]thymidine incorporation of estrogen receptor-deficient MDA-MB-231 breast cancer cells. At 100 µM I3C, proliferation of these cells was inhibited by greater than 50%. Western blot analysis using antibodies to the human estrogen receptor confirmed that the MDA-MB-231 breast cancer cells used in this assay do not express an estrogen receptor protein, while, MCF7 cells produce estrogen receptors. I3C effects on estrogen receptor (ER) function was monitored by transient transfection of an ERE-vit-CAT reporter plasmid containing the vitellogenin promoter with three estrogen response elements linked upstream and driving the bacterial chloramphenicol acetyl transferase (CAT) gene. MCF7 breast cancer cells were transiently transfected by the lipofectamine procedure and, after 48 hours of treatment with the indicated steroids and/or I3C, reporter gene activity was assayed by monitoring the conversion of [$^3$H]acetyl-CoA (plus unlabeled chloramphenicol) into [$^3$H] acetylchloramphenicol using a quantitative non-chromatographic extraction procedure we have optimized (22, 23). MCF7 cells were cultured in 10% fetal bovine serum which is the conditions that we observe the antiproliferative effects of I3C. Fetal bovine serum has endogenous estrogen at a sufficient concentration to cause a high basal level of reporter gene activity in MCF7 cells transiently transfected with the ERE-vit-CAT reporter plasmid. 100 nM estrogen stimulated ERE-vit-CAT activity, whereas, tamoxifen inhibited the basal ERE-vit-CAT reporter plasmid activity by 70%. Treatment with I3C had no effect on the estrogen receptor responsiveness of the ERE-vit-CAT activity nor did this dietary indole modulate the antagonistic effects of tamoxifen.

I3C Induces a G1 Cell Cycle Arrest of MCF-7 Breast Cancer Cells and Abolishes the Production of the CDK6 Cell Cycle Component In normal mammary epithelial cells an intricate network of growth inhibitory and stimulatory signals transduced from the extracellular environment converge on G1 acting components which, through their concerted actions, stringently regulate cell cycle progression (24–26). The final targets of these growth signaling pathways are specific sets of cyclin-cyclin dependent kinase (CDK) complexes, which function at discrete, but overlapping, stages of the cell cycle (24–27). Within the G1 phase of the cell cycle, certain cyclins (C, D1, D2, D3, E) activate the G1 CDKs (CDK2, 3, 4, and 6), while, in a complementary manner, several of the small proteins associated with cyclin-CDK complexes (p15, p16/Ink4, p21/Waf1/Cip1, cip2, p27) have been shown to act as specific inhibitors of cyclin dependent kinase activity and block cell cycle progression within G1 or early S phase (25, 26, 28). In contrast to normal cells, the loss of cell cycle control in G1 has been implicated in mammary tumor development and proliferation. Approximately 40% of human breast cancers show an aberrant expression and/or amplification of cyclin D1 or cyclin E (29–31). Mammary tumors can also display an inappropriate expression and/or mutation of certain G1-acting proto-oncogenes (32, 33), of growth factors and their cognate receptors which stimulate progression through the G1 phase (34–36) and can exhibit a loss in expression or function of certain tumor-suppressor genes (such as p53) which modulate cell cycle events late in the G1 phase (37, 38).

Regulated changes in the expression and/or activity of cell cycle components that act within G1 have been associated with alterations in the proliferation rate of normal and transformed mammary epithelial cells (39–43). For example, estrogens and progesterone stimulate, and anti-estrogens inhibit, cell cycle progression of the T47D human breast cancer cell line at a point in early G1 phase of the cell cycle with corresponding changes in cyclin D1 expression (39). Also, we have established that glucocorticoids induce a G1 cell cycle arrest and alter expression of cell cycle-regulated genes of rat tumor cells derived from DMBA-induced mammary adenocarcinomas (44).

To assess the cell cycle effects of I3C, MCF-7 cells treated with or without 100 $\mu$M I3C for 96 hours were hypotonically lysed in the presence of propidium iodide to fluorescently stain the nuclear DNA. Flow cytometry profiles of nuclear DNA content revealed that I3C induced a cell cycle arrest of these breast cancer cells. I3C treatment altered the DNA content of the MCF7 cell population from an asynchronous population of growing cells in all phases of the cell cycle (29% in G1/G0; 50% in S phase and 21% in G2/M phase) to one in which most (75%) of the I3C treated breast cancer cells exhibited a 2n DNA content, which is indicative of a G1 block in cell cycle progression. In addition, after 96 hours of I3C treatment, approximately 13% of the cells remained with a G2/M DNA content. Preliminary characterization of cell cycle kinetics after I3C withdrawal suggests that the primary I3C-mediated cell cycle block occurs early in the G1 phase. This observation that I3C, and not one of its acid breakdown products, induces a G1 cell cycle arrest of human breast cancer cells is a previously uncharacterized growth response to dietary indoles.

To determine the mechanism by which I3C induces the G1 cell cycle arrest of human breast cancer cells, Western blot and Northern blot analyses were utilized to examine whether I3C treatment regulates the protein production and transcript expression of the cyclin dependent protein kinases (CDKs), cyclins and CDK Inhibitor components of the cell cycle that function within the G1 phase. Most significantly, we have discovered that I3C rapidly reduces the level of CDK6 protein within 24 hours of indole treatment, which is 48 hours prior to the complete cell cycle arrest. In particular, CDK6 transcript levels dropped about 30% in 5 hrs and 60% by 15 hours. In addition, dose response experiments demonstrated that CDK6 levels are reduced to the same extent as the inhibition of DNA synthesis implicating a causal relationship between these two effects of I3C. Under these conditions, no effect on CDK2 or CDK4 expression was detected, which demonstrates the specificity of this response. Furthermore, I3C inhibits CDK6 protein expression in estrogen receptor negative cell lines. The existence of CDK6 is a relatively recent discovery (45), and our results indicate that the I3C mediated cell cycle arrest is results from the rapid reduction in CDK6 protein levels. This novel observation provides a basis for a molecular diagnostic assay to determine the sensitivity of a given tumor sample to I3C growth suppression.

Western blot analysis has shown that I3C stimulates the level of the p21 cell cycle inhibitor by approximately 3–4 fold only after 72–96 hours of indole treatment, which is when the cells begin to display their maximal cell cycle arrest. This response is not likely to initiate the cell cycle arrest, though provides another useful molecular marker to in the examination of tissue biopsies.

Antiproliferative Effects of a Combination of I3C and the Anti-Estrogen Tamoxifen on Breast Cancer Cell Growth Estrogen receptor (ER)-containing MCF7 or ER-deficient MDA-MB-231 breast cancer cells were treated for 48 hours with 100 $\mu$M I3C or 10 $\mu$M tamoxifen alone or with a combination of both reagents, and [$^3$H]thymidine incorporation used as a measure of cell proliferation. Tamoxifen or I3C inhibited MCF7 DNA synthesis by approximately 60% and 70%, respectively, compared to vehicle controls. Interestingly, a combination both I3C and tamoxifen inhibited [$^3$H]thymidine incorporation by greater than 90% which represents a more stringent growth inhibitory effect than that observed with exposure to either compound alone. In ER-deficient MDA-MB-231 cells, tamoxifen had no growth inhibitory effects under conditions in which I3C exerted a strong growth suppression effect. The effects of a combination of tamoxifen and I3C on these ER-deficient breast cancer cells were equivalent that observed with I3C added alone, which further implicates that I3C can inhibit breast tumor cell growth in an estrogen independent manner. Flow cytometry profiles of nuclear DNA content revealed that a combination of tamoxifen and I3C stimulated a slightly greater percentage of MCF7 cells to arrest in G1 (85%) compared to that observed with either I3C (75%) or tamoxifen (70%) alone. The more stringent cell cycle arrest of MCF7 breast cancer cells by a combination of tamoxifen and I3C is likely due to a disruption of two distinct pathways, an estrogen receptor dependent proliferative pathway disrupted by tamoxifen and an estrogen receptor-independent antiproliferative pathway induced by I3C.

Western blot analysis of the breast cancer cells treated with combinations of I3C and/or tamoxifen demonstrated that I3C, but not tamoxifen, reduced the level of CDK6 protein. Moreover, other studies have shown that tamoxifen reduces cyclin D1 levels in estrogen responsive breast cancer cells (39). The selective regulation of CDK6 by I3C provides a molecular basis for the synergistic actions of a combination of I3C and tamoxifen on the growth suppression of human breast cancer cells since both antiproliferative agents target different components of the cell cycle. Our observations indicate that a combination of I3C and either steroidal or nonsteroidal anti-estrogens (such as tamoxifen, ICI 164384 and raloxifene) provides and advantageous combination hormone based therapy to control breast cancer cell growth.

REFERENCES

1. Sharma, S., et al. (1994) *Cancer Research* 54: 5848–5855.
2. Wattenberg, L. W. and Loub, W. D. (1978) *Cancer Res.* 38: 1410–1415.
3. Grubbs, C. J., et al. (1995) *Anticancer Research,* 15: 709–716.
4. Wattenberg, L. W. (1990) In: *Antimutagenesis and Anticarcinogenesis Mechanisms II*, Kuroda, Y., Shankel, D. M., and Waters, M. D., Eds., Plenum Press, New York. 105–130.
5. Bradlow, H. L., et al. (1991). *Carcinogenesis* 12: 1571–1574.
6. Shertzer, H. G. (1984) *Chemico-Biol. Interactions* 48: 81–90.
7. Bailey, G. S., et al. (1987). *J. Natl. Cancer Inst.* 78: 931–936.
8. Shertzer, H. G. (1983) *Food Chem. Toxicol.* 21: 31–36.
9. Safe, S. H. (1994) *Environ. Sci. & Pollution Res.* 1, 29–33.
10. Lubet, R. National Cancer Institute, personal communication to L. Bjeldanes
11. Michnovicz, J. J. and Bradlow, H. L. (1990) *J. Natl. Cancer Inst.* 82: 947–951.
12. Jellinck, P. H., et al. (1993) *Biochem. Pharmacol.* 43: 1129–1136.
13. Tiwari, R. K., et al. (1994) *J. Natl. Cancer Inst.* 86: 126–131.
14. de Kruif, C. A., et al. (1991) *Chem.-Biol. Interact.* 80: 303–315.
15. Grose, K. R., and Bjeldanes, L. F. (1992) *Chem. Res. Toxicol.* 5: 188–193.
16. Bradfield, C. A. and Bjeldanes, L. F. (1987). *J. Toxicol. Environ. Health* 21: 311–323.
17/18. Bjeldanes, L. F., et al. (1991). *Proc. Natl. Acad. Sci USA* 88: 9543–9547.
19. Kwon, C.-S., et al. (1994) *J. Agr. Food Chem.* 42: 2536–2540.
20. Liu, H., et al. (1994) *J. Natl. Cancer Inst.* 86: 1758–1765.
21. Chen, Y.-H., et al. (1995) *J. Biol. Chem.* 270: 22548–22555.
22. Webster M. K., et al. (1993) *Mol Cell Biol* 13: 2031–2040.
23. Maiyar, A. C., et al. (1996) *J. Biol. Chem.* 271: 12414–12422.
24. Draetta G. F. (1994) Mammalian G1 cyclins. *Curr Opin Cell Biol* 6: 842–846.
25. Elledge S. J., Harper J. W. (1994) *Curr Opin Cell Biol* 6: 847–852.
26. Hunter T., Pines J (1994) *Cell* 79: 573–582.
27. Solomon M. J. (1993) *Curr Opin Cell Biol* 5: 180–186.
28. Peter M, Herskowitz I (1994) *Cell* 79: 181–184.
29. Lammie G. A., etal. (1991) *Oncogene* 6: 439–444.
30. Schuuring E., Verhoeven E, Mooi W J, Michalides R J (1992) *Oncogene* 7: 355–361.
31. Keyomarsi K., Pardee A B (1993) *Proc Natl Acad Sci USA* 90: 1112–1116.
32. Kumar R., Medina D, Sukumar S (1990) *Oncogene* 5: 1271–1277.
33. Kreipe H, et al. (1993) *Cancer Res* 53: 1956–1961.
34. Pardee A. B. (1989) G1 events and regulation of cell proliferation. *Science* 246: 603–608.
35. Aaronson S. A. (1991) *Science* 254: 1146–1153.
36. Klijn J. G., Berns P M, Schmitz P I, Foekens J A (1992) *Endocr Rev* 13: 3–17.
37. Weinberg R. A. (1991) Tumor suppressor genes. *Science* 254: 1138–1146.
38. Jerry D. J., et al. (1993) *Cancer Res* 53: 3374–3381.
39. Musgrove E. A., et al. (1993) *Mol Cell Biol* 13:3577–3587.
40. Dickson, R. B. and Lippman, M. E. (1995) *Endocrine Reviews* 16: 559–589.
41. Leung B. S., Potter A H (1987) *J Cell Biochem* 34: 213–225.
42. Musgrove E. A., Lee C S, Sutherland R L (1991) *Mol Cell Biol* 11: 5032–5043.
43. Musgrove E. A., Wakeling A E, Sutherland R L (1989) *Cancer Res* 49: 2398–2404.
44. Goya L., Maiyar A C, Ge Y, Firestone G L (1993) *Mol Endocrinol* 7: 1121–1132.
45. Meyerson, M., and Harlow, E. (1994) *Molec. Cell. Biol.* 14: 2077–2086.
46. Leete, E. and Marion, L. (1953) *Can. J. Chem.* 31: 775–784.
47. Leete, E. (1959) 3-Hydroxymethylindoles. *J. Amer. Chem. Soc.* 81: 6023–6026.
48. Ruangyuttikarn, W., Skiles, G. and Yost, G. (1992) *Chem. Res. Toxicol.* 5: 713–719.
49. Monde, K., Takasugi, M. and Ohnishi, T. (1994) *J. Amer. Chem. Soc.* 116: 6650–6657.
50. Takasugi, M., et al. (1988) *Bull. Chem. Soc. Jpn.,* 61: 285–289.
51. Alexander D. B., et al. (1993) *Cancer Res* 53: 1808–1815.
52. Yang, N. N., et al. (1996) *Science* 273: 1222–1225.
53. Goya L., et al. (1993) *Cancer Res* 53: 1816–1822.
54. Goya L., Edwards C P, Glennemeier K A, Firestone G L (1991). *Cancer Lett* 58: 211–219.
55. Muss, H. B. (1992) *Breast Cancer Research and Treatment* 21: 15–26.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of inhibiting tumor cell growth comprising contacting a target tumor cell with, or administering to an individual in need thereof, an effective amount of an indole-3-carbinol compound or a derivative thereof, wherein said compound is stable in acidic aqueous solution, said inhibition is estrogen-independent and said compound is not indole-3-carbinol, 3,3'-diindolylmethane or indole carbazole.

2. A method for evaluating the growth inhibitory activity of an I3C deriviative, said method comprising the steps of:

contacting a cell with an effective amount of an I3C derivative;

measuring the CDK6 expression in said cell; and evaluating said activity, wherein the reduction in CDK6 expression is correlated with the growth inhibitory activity of said compound.

3. The method of claim 2 wherein said growth inhibitory activity is estrogen-independent.

* * * * *